United States Patent
Shammas (10) Patent No.: US 10,555,667 B2
(45) Date of Patent: Feb. 11, 2020

(54) SYSTEM AND METHOD FOR DETERMINING INTRAOCULAR LENS POWER

(71) Applicant: Hanna Shammas, Los Angeles, CA (US)

(72) Inventor: Hanna Shammas, Los Angeles, CA (US)

(*) Notice: Subject to any disclaimer, the term of this patent is extended or adjusted under 35 U.S.C. 154(b) by 0 days.

(21) Appl. No.: 16/367,104

(22) Filed: Mar. 27, 2019

(65) Prior Publication Data

US 2019/0216314 A1  Jul. 18, 2019

Related U.S. Application Data

(62) Division of application No. 14/613,225, filed on Feb. 3, 2015, now Pat. No. 10,278,574.

(60) Provisional application No. 61/935,004, filed on Feb. 3, 2014.

(51) Int. Cl.
*A61B 3/10* (2006.01)
*A61B 3/107* (2006.01)
*A61F 9/007* (2006.01)
*A61F 2/16* (2006.01)

(52) U.S. Cl.
CPC ............ *A61B 3/1005* (2013.01); *A61B 3/107* (2013.01); *A61F 9/007* (2013.01); *A61F 2/16* (2013.01)

(58) Field of Classification Search
CPC .................................... A61F 2/14; A61F 2/16
USPC ....... 351/159.73–159.77; 606/4, 5; 623/6.11, 623/6.12, 6.13
See application file for complete search history.

(56) References Cited

U.S. PATENT DOCUMENTS

| | | |
|---|---|---|
| 5,282,852 A | 2/1994 | Capetan et al. |
| 5,676,669 A | 10/1997 | Colvard |
| 7,044,604 B1 | 5/2006 | Arrowsmith |
| 7,303,281 B2 | 12/2007 | Wakil et al. |
| 7,490,938 B2 | 2/2009 | Latkany |
| 8,096,658 B2 | 1/2012 | Kikawa et al. |
| 8,182,088 B2 | 5/2012 | Norrby et al. |
| 8,210,683 B2 | 7/2012 | Geggel |
| 8,231,672 B2 | 7/2012 | Deacon et al. |
| 8,241,353 B2 | 8/2012 | Deacon et al. |
| 8,475,439 B2 | 7/2013 | Van Heugten et al. |
| 2008/0231809 A1 | 9/2008 | Haigis |
| 2010/0211167 A1 | 8/2010 | Glazier |
| 2010/0324543 A1 | 12/2010 | Kurtz et al. |
| 2011/0015541 A1 | 1/2011 | Padrick et al. |
| 2011/0242482 A1 | 10/2011 | Olsen |

(Continued)

OTHER PUBLICATIONS

Shammas, H. John, Chapter 1: Basic Optics for Intraocular Lens Power Calculations, Intraocular Lens Power Calculations, 2004, pp. 1-5, Slack Inc. Publishers, Thorofare, NJ.

*Primary Examiner* — Robert E. Tallman
(74) *Attorney, Agent, or Firm* — Milord A. Keshishian (57) ABSTRACT

The present invention discloses systems and methods for determine preoperative estimation of postoperative IOL position (or the EAPD) in accordance with one or both of the following mathematical relationships, which are derived from linear regression:

$$EAPD = S_1 + (S_2 \times AND) + (S_3 \times NT) + (S_4 \times AL), \quad (1a)$$

$$EAPD = W_1 + (W_2 \times AND) + (W_3 \times RND) + (W_4 \times AL), \quad (1b)$$

where $S_1$, $S_2$, $S_3$, and $S_4$ for equation (1a) and $W_1$, $W_2$, $W_3$, and $W_4$ for equation (1b) are statistically derived linear regression constant coefficients.

12 Claims, 7 Drawing Sheets

(56) References Cited

U.S. PATENT DOCUMENTS

| | | |
|---|---|---|
| 2012/0044454 A1 | 2/2012 | Canovas Vidal et al. |
| 2012/0155726 A1 | 6/2012 | Li et al. |
| 2012/0158132 A1 | 6/2012 | Canovas Vidal et al. |
| 2013/0050641 A1* | 2/2013 | Van Der Mooren ............... A61B 3/0025 351/159.74 |
| 2013/0100408 A1 | 4/2013 | Simpson |
| 2013/0235343 A1 | 9/2013 | Hee et al. |

* cited by examiner

Figure 3A-1
Scattergram comparing the difference between the APD and the AND values to the nucleus thickness

Figure 3A-2

Scattergram comparing the difference between the APD and the AND values to the retro-nucleus distance (RND)

Figure 3C

Scattergram comparing the calculated EAPD to the post-operative measured APD

SYSTEM AND METHOD FOR DETERMINING INTRAOCULAR LENS POWER

CROSS-REFERENCE TO RELATED APPLICATIONS

This application is a DIVISIONAL U.S. Non-Provisional Utility application that claims the benefit of priority of the U.S. Non-provisional Utility application Ser. No. 14/613,225 with filing date Feb. 3, 2015, which claims the benefit of priority of U.S. Utility Provisional Patent Application No. 61/935,004, filed Feb. 3, 2014, the entire disclosures of all of which applications are expressly incorporated by reference in their entirety herein.

It should be noted that where a definition or use of a term in the incorporated patent application is inconsistent or contrary to the definition of that term provided herein, the definition of that term provided herein applies and the definition of that term in the incorporated patent application does not apply.

BACKGROUND OF THE INVENTION

Field of the Invention

One or more embodiments of the present invention relate to intraocular lenses (IOL) and more particularly, to systems and methods for determining or selection of intraocular lens (IOL) power.

Description of Related Art

It is obvious that a more precise determination of IOL estimated power ($IOL_{EP}$) is an important aspect in providing the appropriate eyesight (e.g., emmetropia, ametropia, etc.) for a subject for a desired vision. In general, measurements of the eye are typically made preoperatively and an IOL estimated power (or $IOL_{EP}$) is selected based on correlations between the measured values and different lens powers providing an estimated refractive outcome.

Most commonly used formulas for IOL power calculations for an appropriate refractory outcome require the preoperative estimation of postoperative IOL position, known as Estimated Lens (i.e., IOL) Position (or ELP), which is a function of where the IOL would be positioned inside the eye. It is well known that ELP is the largest contributor of error in the refractive outcome (or the $IOL_{EP}$). Another term for the estimated IOL lens position (ELP) is the Estimated Anterior Pseudophakic Distance (or EAPD). The term Anterior Pseudophakic Distance (or APD) may be defined as the postoperative, actual distance from the anterior surface of the cornea to the anterior surface of the IOL, with EAPD being the estimated, preoperative measurement.

Accordingly, in light of the current state of the art and the drawbacks to current system and methodologies for determining IOL power, the need exists for a system and method that would enable a more precise determination of EAPD to thereby facilitate a more precise determination or selection of $IOL_{EP}$ estimated power for a more precise refractive outcome.

BRIEF SUMMARY OF THE INVENTION

A non-limiting, exemplary aspect of an embodiment of the present invention provides a method for determine preoperative estimation of postoperative IOL position, comprising:
determining an axial length (AL) of an eye;
determining Ante-Nucleus Distance (AND), which is a distance from an anterior surface of cornea along an optical axis of the eye to an anterior surface of a natural lens nucleus;
determining Retro-Nucleus Distance (RND), which is a distance from an anterior surface of the natural lens nucleus to a posterior surface of a natural lens capsule;
with an Estimated Anterior Pseudophakic Distance (EAPD) calculated according:

$$EAPD = W_1 + (W_2 \times AND) + (W_3 \times RND) + (W_4 \times AL),$$

Where $W_1$, $W_2$, $W_3$, and $W_4$ are constant coefficients.

Another non-limiting, exemplary aspect of an embodiment of the present invention provides method for determine preoperative estimation of postoperative IOL position, comprising:
determining an axial length (AL) of an eye;
determining Ante-Nucleus Distance (AND), which is a distance from an anterior surface of cornea along an optical axis of the eye to an anterior surface of a natural lens nucleus;
determining natural lens Nucleus Thickness (NT), which is a distance measured along an optical axis from an anterior surface of a lens nucleus to a posterior surface of the lens nucleus;
with an Estimated Anterior Pseudophakic Distance (EAPD) calculated according:

$$EAPD = S_1 + (S_2 \times AND) + (S_3 \times NT) + (S_4 \times AL),$$

Where $S_1$, $S_2$, $S_3$, and $S_4$ are constant coefficients.

Such stated advantages of the invention are only examples and should not be construed as limiting the present invention. These and other features, aspects, and advantages of the invention will be apparent to those skilled in the art from the following detailed description of preferred non-limiting exemplary embodiments, taken together with the drawings and the claims that follow.

BRIEF DESCRIPTION OF THE DRAWINGS

It is to be understood that the drawings are to be used for the purposes of exemplary illustration only and not as a definition of the limits of the invention. Throughout the disclosure, the word "exemplary" may be used to mean "serving as an example, instance, or illustration," but the absence of the term "exemplary" does not denote a limiting embodiment. Any embodiment described as "exemplary" is not necessarily to be construed as preferred or advantageous over other embodiments. In the drawings, like reference character(s) present corresponding part(s) throughout.

FIG. 3A-1 is a non-limiting, exemplary illustration of scattergram chart, comparing the differences between the post-operative APD and the pre-operative AND values to the NT in accordance with one or more embodiments of the present invention;

FIG. 3A-2 is a non-limiting, exemplary illustration of scattergram chart, comparing the differences between the post-operative APD and the pre-operative AND values to the RND in accordance with one or more embodiments of the present invention;

DETAILED DESCRIPTION OF THE INVENTION

The detailed description set forth below in connection with the appended drawings is intended as a description of presently preferred embodiments of the invention and is not intended to represent the only forms in which the present invention may be constructed and or utilized.

The present invention provides systems and methods that enable a more precise determination of preoperative estimation of postoperative IOL position (the EAPD) to thereby facilitate a more precise determination or selection of $IOL_{EP}$ estimated power for a more precise refractive outcome.

Figure 1A:
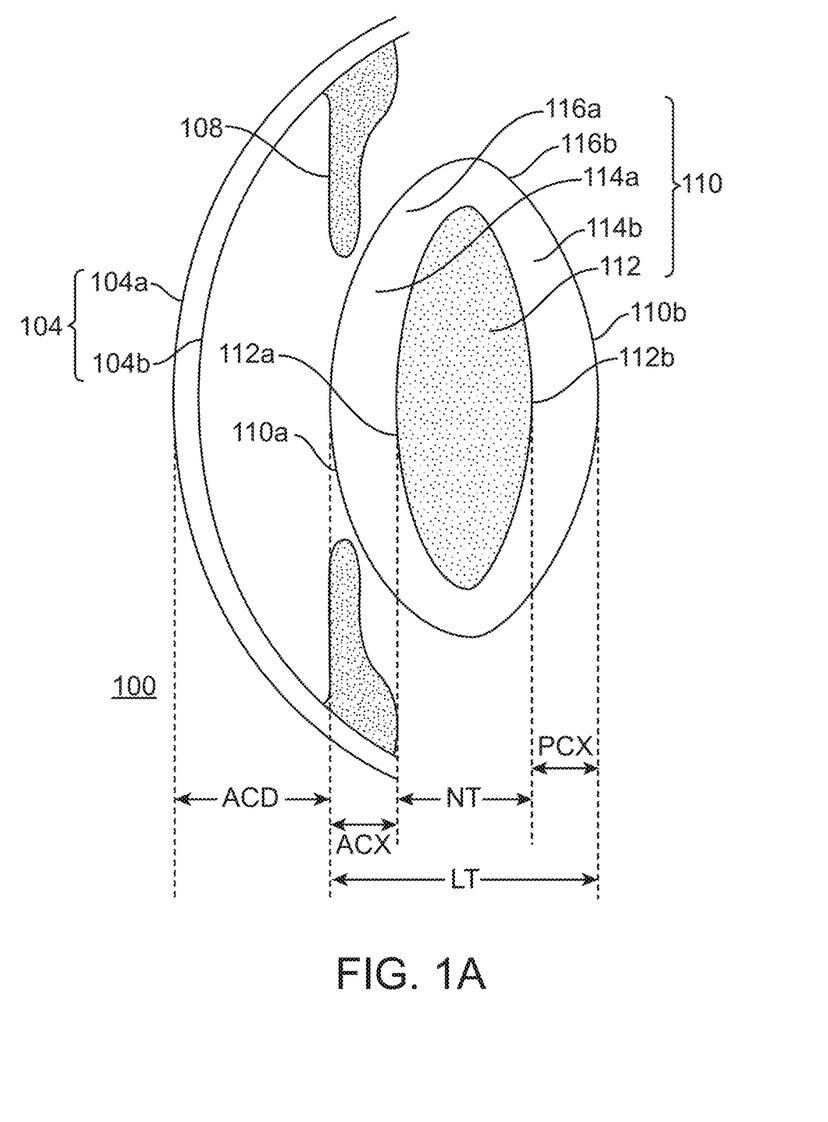
FIG. 1A is a non-limiting, exemplary schematic illustration of a sectional profile of an eye, including different distances that are measured in accordance with one or more embodiments of the present invention.

FIG. 1A is a non-limiting, exemplary schematic illustration of a cross-sectional profile of different structures of an eye (where the natural lens is still in place), and different distances that are measured in accordance with one or more embodiments of the present invention. The overall anatomy of the eye is very well known and hence, various ophthalmic structures of the phakic eye 100 in FIG. 1A will be described in view of the distances measured.

As illustrated in FIG. 1A, in general, the natural lens 110 (with anterior surface 110a and posterior surface 110b) is comprised of a lens nucleus 112 (with anterior surface 112a and posterior surface 112b) that is a surrounded by a lens cortex 114 (with anterior surface 114a and posterior surface 114b), encapsulated within a lens capsule 116 (with anterior surface 116a and posterior surface 116b), forming the natural lens 110. In other words, the lens nucleus 112 of the natural lens 110 is fully surrounded within a cortical material (soft material that comprise or form the lens cortex 114), with both the lens nucleus 112 and its surrounding lens cortex 114 secured (or encapsulated) within the lens capsule 116. In most cases, it is the lens cortex 114 (the anterior surface 114a of the lens cortex 114) that is mostly affected in terms of significant variations or changes in its shape due to any number of ophthalmic issues such as cataract, which, in turn, affects the shape of the lens capsule 116 and somewhat the lens nucleus 112. This, in turn, affects the refractory outcome of the eye.

Anterior cortical deformations in particular, introduce significant errors to the conventional EAPD measurements and specifically, to EAPD measurements that rely on the span of the Anterior Chamber Depth (ACD). The ACD is defined, as a distance measured along an optical axis from the anterior surface 104a of the cornea 104 to the anterior surface 110a of the natural lens 110, which is the anterior surface 116a of the lens capsule 116 behind (or within) which, may be a deformed lens cortex 114 (the anterior portion 114a). This deformation of the lens cortex 114 makes the ACD parameter for calculating a more precise EAPD unreliable.

Further, in most instances (including in those with cataract eye), the lens cortex 114 and the lens nucleus 112 are removed (known as phacoemulsification) from the lens capsule 116, which cause the capsule 116 to collapse, making measurements with respect to natural Lens Thickness (LT) useless, in particular when accounting for the fact that the replacement IOL has a different dimension than the LT of the natural lens 110 and further, may be positioned within the lens capsule 116 at a different focal position. The present invention defines natural lens thickness LT as the distance measured along an optical axis from the anterior lens capsule surface 116a to the posterior lens capsule surface 116b of the natural lens 110, which includes the lens cortex 114 and the lens nucleus 112. Accordingly, both ACD and LT measurements are at best very rough approximations, introducing significant errors to the overall calculations for EAPD and hence, eventually IOL power due to deformities of the lens cortex 114.

Figure 2:
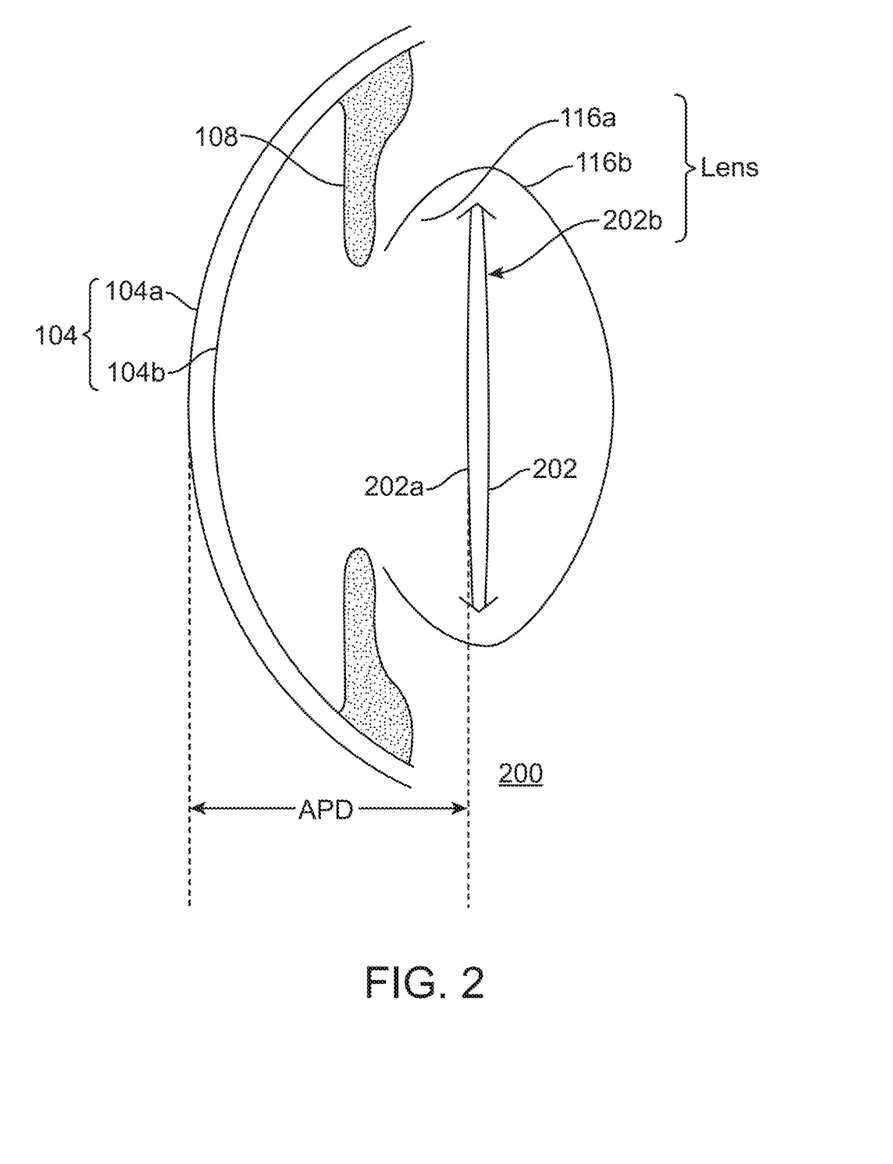
FIG. 2 is a non-limiting, exemplary schematic illustration of a cross-sectional profile of the anterior segment of a pseudophakic eye in accordance with one or more embodiments of the present invention.

FIG. 2 is a non-limiting, exemplary schematic illustration of a cross-sectional profile of the anterior segment of a pseudophakic eye (where the natural lens is replaced by IOL). As illustrated and further described below, one or more embodiments of the present invention incorporate new measurements that provide a superior prediction of an Anterior Pseudophakic Distance (APD) with more precise results (shown in FIG. 2) of $IOL_{EP}$ estimated power. As indicated above and now in relation to FIG. 2, APD may be defined as the postoperative, actual distance from the anterior surface 104a of the cornea 104 to the anterior surface 202a of the IOL 202. APD may be measured in a variety of different ways after surgery, non-limiting example of which may include the use of the well-known LENSTAR LS 900® by HAAG-STREIT DIAGNOSTICS from Switzerland.

Referring back to FIG. 1A, as indicated above, in order to calculate, determine, or estimate the power of IOL 202 (FIG. 2) that is able to provide a predetermined refractive outcome, various dimensions or measurements of the eye 100 are made prior to the surgical procedure. Various ophthalmic measurements in accordance with the present invention may be performed using any number of well known conventional machines (optical or ultrasound). A non-limiting example of an optical biometric machine that may be used for determining various ophthalmic measurements may include the above mentioned LENSTAR LS 900® by HAAG-STREIT DIAGNOSTICS from Switzerland. It should be noted that the various ophthalmic measurements in accordance with the present invention may be performed and obtained using one-dimensional calculations (linearly along an optical axis, best shown in FIG. 1B, which were obtained using LENSTAR LS 900®) or in two-dimensions (planer imagery).

As illustrated in FIGS. 1A to 3C, the present invention provides systems and methods for determine preoperative estimation of postoperative IOL position (or the EAPD) in accordance with one or both of the following mathematical relationships, which are derived from linear regression:

$$EAPD = S_1 + (S_2 \times AND) + (S_3 \times NT) + (S_4 \times AL), \quad (1a)$$

$$EAPD = W_1 + (W_2 \times AND) + (W_3 \times RND) + (W_4 \times AL), \quad (1b)$$

where $S_1$, $S_2$, $S_3$, and $S_4$ for equation (1a) and $W_1$, $W_2$, $W_3$, and $W_4$ for equation (1b) are statistically derived linear regression constant coefficients (detailed below). The calculations of EAPD using equation (1a) are based on measurements of the Axial Length (or AL), Ante-Nucleus Distance (or AND that is further detailed below), and natural lens Nucleus Thickness (or NT that is further detailed below), and calculations using equation (1b) are based on measurements of the AL, AND, and Retro-Nucleus Distance (or RND that is further detailed below).

As detailed below, both of the EAPD equations (1a) and (1b) are statistically equal and as indicated below, may be equally (at least statistically equally) used to determine the estimated $IOL_{EP}$ power. However, which EAPD equation ((1a) and or (1b)) to use depends on the type of optical biometric machine being used and whether the optical biometric machine is capable of determining the values of the variables in equations (1a) or (1b). For example, certain optical biometric machines can directly calculate the values of NT in which case, equation (1a) may be used and others, may not have the capability to directly measure NT in which case, equation (1b) may be used. Accordingly, the type of EAPD equation (1a) and or (1b) used is dictated by the capability limits of the optical biometric machine.

Referring to equations (1a) and (1b), AL in equations (1a) and (1b) is defined as a distance from an anterior surface 104a of cornea 104 along an optical axis of the eye 100 to an anterior surface of the retina 118 within a fovea region of the eye. The optical axis is a reference line along which light propagates through the eye. AND in equations (1a) and (1b) is a distance from an anterior surface 104a of cornea 104 along an optical axis of the eye 100 to an anterior surface 112a of a natural lens nucleus 112, thus advantageously bypassing the irregularities associated with the anterior portion 114a of the natural lens cortex 114. The prefix "ante" in AND is referring to the space or span that is located before the natural lens nucleus 112 or preceding the natural lens nucleus 112. Another advantage of AND measurement is that the overall EAPD is determined from a closer distance or nearer to the position where the IOL would replace the natural lens 112, which is the anterior surface 112a of the nucleus 112 of the natural lens 110, rather than approximations from a farther distance of anterior surface 116a of the lens capsule 116. That is, estimating the preoperative position of the IOL nearer to where the postoperative position of IOL would be positioned is within a more confined space occupied by the natural lens nucleus 112 (resulting in a more precision approximation) rather than the more expansive space occupied by the entire natural lens 110 that may also include a deformed lens cortex 114.

The AND in equations (1a) and (1b) may be determined as follows:

$$AND = ACD + ACX, \quad (2)$$

where ACD in equation (2) is the Anterior Chamber Depth, defined as a distance from an anterior surface 104a of cornea 104 along an optical axis of the eye 100 to an anterior surface 110a of the natural lens 110 (which is the anterior surface 116a of the lens capsule 116). The ACX in equation (2) is the Anterior Cortical Space defined by a distance from the anterior surface 110a of the natural lens 110 (which is the anterior surface 116a of the lens capsule 116) along an optical axis of the eye 100 to the anterior surface 112a of the lens nucleus 112. In general, if the AND value is shallow (closer to the cornea 104 along the optical axis), the IOL approximate anterior position will most likely be predicatively positioned closer towards the cornea 104 and if AND value is longer (has more depth), the IOL approximate anterior position will most likely be predicatively positioned further from the cornea 104.

The NT in equation (1a) is defined as a distance measured along an optical axis from an anterior surface 112a of the lens nucleus 112 to a posterior surface 112b of the lens nucleus 112. In general, if the NT has a low value (closer to the cornea 104 along the optical axis), the IOL will most likely be predicatively positioned closer towards the cornea 104 and if the NT has a high value, the IOL approximate position will most likely be predicatively positioned further from the cornea 104.

The RND in equation (1b) is a distance from an anterior surface 112a of the natural lens nucleus 112 to a posterior surface 116b of a natural lens capsule 116. The prefix "retro" in RND is referring to span that is located behind nucleus 112 (anterior surface 112a thereof). In general, if the RND has a low value (closer to the cornea 104 along the optical axis), the IOL will most likely be predicatively positioned closer towards the cornea 104 and if the RND has a high value, the IOL approximate position will most likely be predicatively positioned further from the cornea 104.

The RND in equation (1b) may be determined as follows:

$$RND = (NT + PCX) = (LT - ACX), \quad (3)$$

where NT in equation (3) is lens nucleus thickness, which is defined as a distance measured along an optical axis from an anterior surface 112a of the lens nucleus 112 to a posterior surface 112b of the lens nucleus 112. The PCX in equation (3) is the posterior cortical space defined by a distance from the posterior surface 112b of the natural lens nucleus 112 along an optical axis of the eye 100 to the posterior surface 110b of the lens 110 (which is the posterior surface 116b of the lens capsule 116). The LT is the distance measured along an optical axis from the anterior lens capsule surface 116a to the posterior lens capsule surface 116b of the natural lens 110, which includes the lens cortex 114 and the lens nucleus 112. The ACX is the anterior cortical space defined by a distance from the anterior surface 110a of the natural lens 110 (which is the anterior surface 116a of the lens capsule 116) along an optical axis of the eye 100 to the anterior surface 112a of the lens nucleus 112.

It should be noted that since the IOL 202 replaces the natural lens nucleus 112 within the natural lens capsule 116 rather than replacing the entire natural lens 110, determining the position or location of the lens nucleus 112 where the IOL 202 is supposed to be positioned and replace is a more precise measurement than the location of the entire natural lens 110. Therefore, the above AND, NT, and RND measurements estimate the preoperative position of the IOL nearer to where the postoperative position of IOL would be positioned, which is the more confined space occupied by the natural lens nucleus 112 rather than the more expansive (or larger volume of) space occupied by the entire natural lens 110 that may also include a deformed lens cortex 114, providing a substantially improved estimated $IOL_{EP}$ power.

Figure 1B:
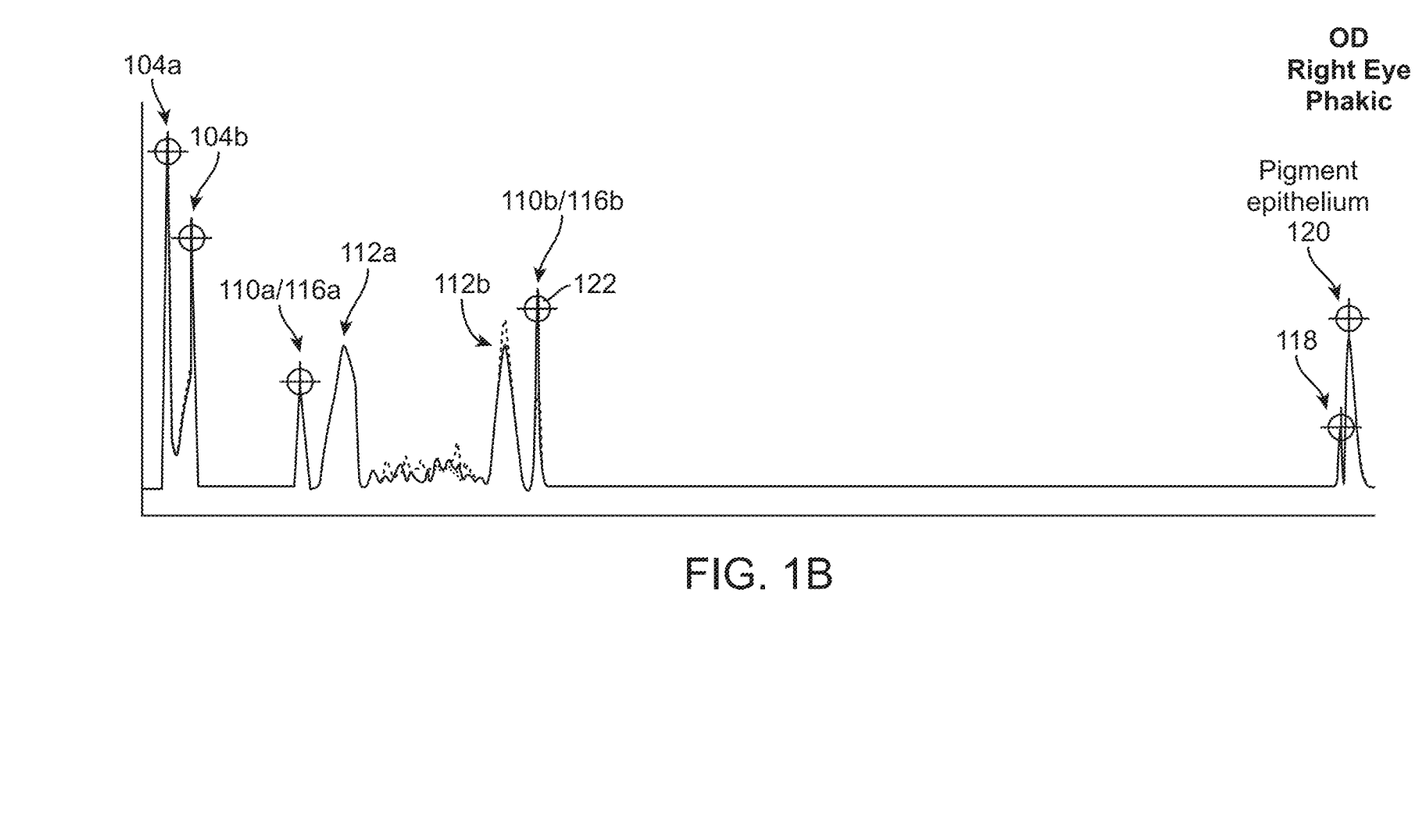
FIG. 1B is a non-limiting, exemplary illustration of a representation of a display of the biometric measurement of eye segments in accordance with one or more embodiments of the present invention.

FIG. 1B is a representative display of the biometric measurement of the different eye segments using the above-mentioned LENSTAR LS 900® biometer. The following illustrated spikes are noted on the graph, identifying from left to right, the anterior surface of the cornea 104a, the posterior surface of the cornea 104b, the anterior surface of the natural lens 110a or anterior surface of lens capsule 116a, the anterior surface of the natural lens nucleus 112a, the posterior surface of the natural lens nucleus 112b, the posterior surface of the natural lens 110b or posterior surface of the lens capsule 116b, the retinal surface 118 and the pigment epithelium layer 120.

The indicators 122 displayed at the tip of the two corneal spikes (104a and 104b), the two natural lens or lens capsule spikes (110a/116a and 110b/116b), the retinal spike (118) and the pigment epithelium layer spike (120) are used to measure distances between the different indicators 122 to automatically generate the axial length of the eye (AL), the anterior chamber depth ACD, and the lens thickness (LT).

In addition to the conventionally measured ophthalmic parameters (of AL, ACD, and LT), additional measurements are further obtained in accordance with one or more embodiments of the present invention. The one or more embodiments of the present invention further determine measurements for the ophthalmic parameters ACX, NT, and PCX to further calculate the AND and the RND, all of which are used in equations (1a) and (1b) above.

The resulting calculated EAPD from equations (1a) or (1b), which is further detailed below, may be used in a number of lens power (or refractive) calculations. The following is one, non-limiting example of IOL power calculations (for discussion purposes) using the well-known thin lens methodology applied to a two-lens system (cornea and IOL). Of course, the resulting EAPD from equations (1a) or (1b) may equally be applied to or used within other well-known IOL power calculation formulas such as those that use ray tracing.

$$IOL_{EP} = \frac{n_{AH}}{AL - EAPD} - \frac{1}{\frac{1}{K + R_C} - \frac{EAPD}{n_{AH}}} \quad (4)$$

In equation (4), $IOL_{EP}$ is the estimated power of IOL, $n_{AH}$ is the index of refraction for the aqueous humor (approximately 1.336), K is corneal power, AL is axial length of the eye, and $R_C$ is refractive error at the corneal plane.

The refractive power of cornea is determined by measuring a radius of curvature of the cornea (CR), and converting the cornea radius into a corneal refractive power K using index of refraction. Corneal power may be determined by a number of well known methods. The present invention used the Scheimpflug principle to more precisely determine the corneal power, which is an index of refraction of 1.329 rather than the standard index of refraction of 1.3375 used by others (see for example H. John Shammas, M D et. al., "Scheimpflug photography keratometry readings for routing intraocular lens power calculation" J Cataract Refract Surg 2009; 35:330-334, which is herein incorporated by reference in its entirety). The refractive error at the corneal plane $R_C$ is the prescription of the glass as if using a contact lens. The advantage of using $R_C$ is that one can add this error to the overall corneal power to estimate the overall power of the $IOL_{EP}$. $R_C = 0$ is used to calculate $IOL_{EP}$ for emmetropia, with $IOL_{EP}$ for ametropia is calculated using the spectacle refraction Rs=Rc/(1+0.012Rc). $R_C$, its calculations, use, and purpose are well known.

Non-Liming Examples

The following discussions are related to determining or deriving specific constants for equations (1a) and (1b), which are based on a limited number of specific case studies. As will be apparent to those skilled in the art, the constants in equations (1a) and (1b) will vary from the below exemplary calculations and be affected depending on many factors, non-limiting, non-exhaustive listing of examples of which may include the model/type of IOL used, the type and the manner in which an ophthalmic surgery is performed, the experience of the physician performing the surgery, whether the phacoemulsification was uneventful or had complications, and etc.

As indicated above, the present invention provides systems and methods for determining preoperative estimation of postoperative IOL position (or the EAPD) in accordance with the above equations (1a) or (1b). Measurements for the ophthalmic parameters AL, AND, RND, and NT in equations (1a) or (1b) may be obtained using the well-known LENSTAR LS 900® biometer. However, the respective constant coefficients of $S_1$, $S_2$, $S_3$, and $S_4$ for equation (1a) and $W_1$, $W_2$, $W_3$, and $W_4$ for equation (1b) are statistically derived. A non-limiting, exemplary statistical analysis that may be used for statistical derivation of the values of the constant coefficients for equations (1a) and (1b) may include the use of linear regression in general, with further evaluations using both single regression and sequential regression. In this non-limiting exemplary instance, the present invention applies linear regression to data (charted in FIGS. 3A to 3C) obtained by evaluating patients that underwent cataract surgery.

The present invention evaluated ninety eyes of 90 consecutive patients with no other ocular pathology who had uneventful phacoemulsification cataract surgery. If both eyes had cataract surgery only the first operated eye was included in the study to avoid data duplication. The inventor of the present invention performed all surgeries. An acrylic IOL (SN60WF, ALCON SURGICAL, INC.™) was placed in the lens capsule 116 in all cases. The final refraction was obtained 4 to 5 weeks after cataract surgery. That is, approximately one month after surgery, the APD was measured with an optical biometric machine. The post-operative APD was then compared to the AL, ACD, LT, K, NT, RND, and AND (all measured before the surgery) through regression equations (detailed below).

Figure 3A:
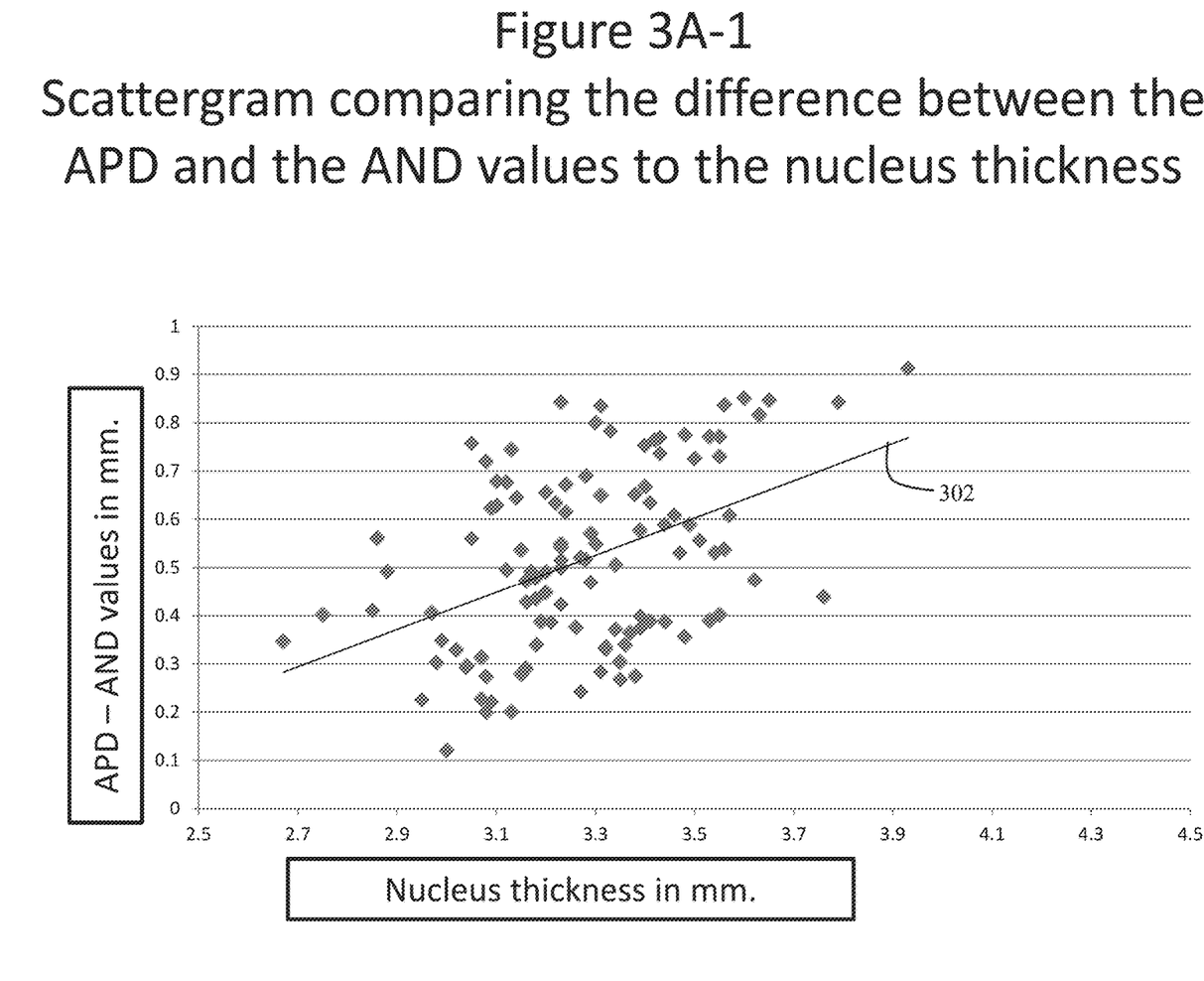
Figure 3A:
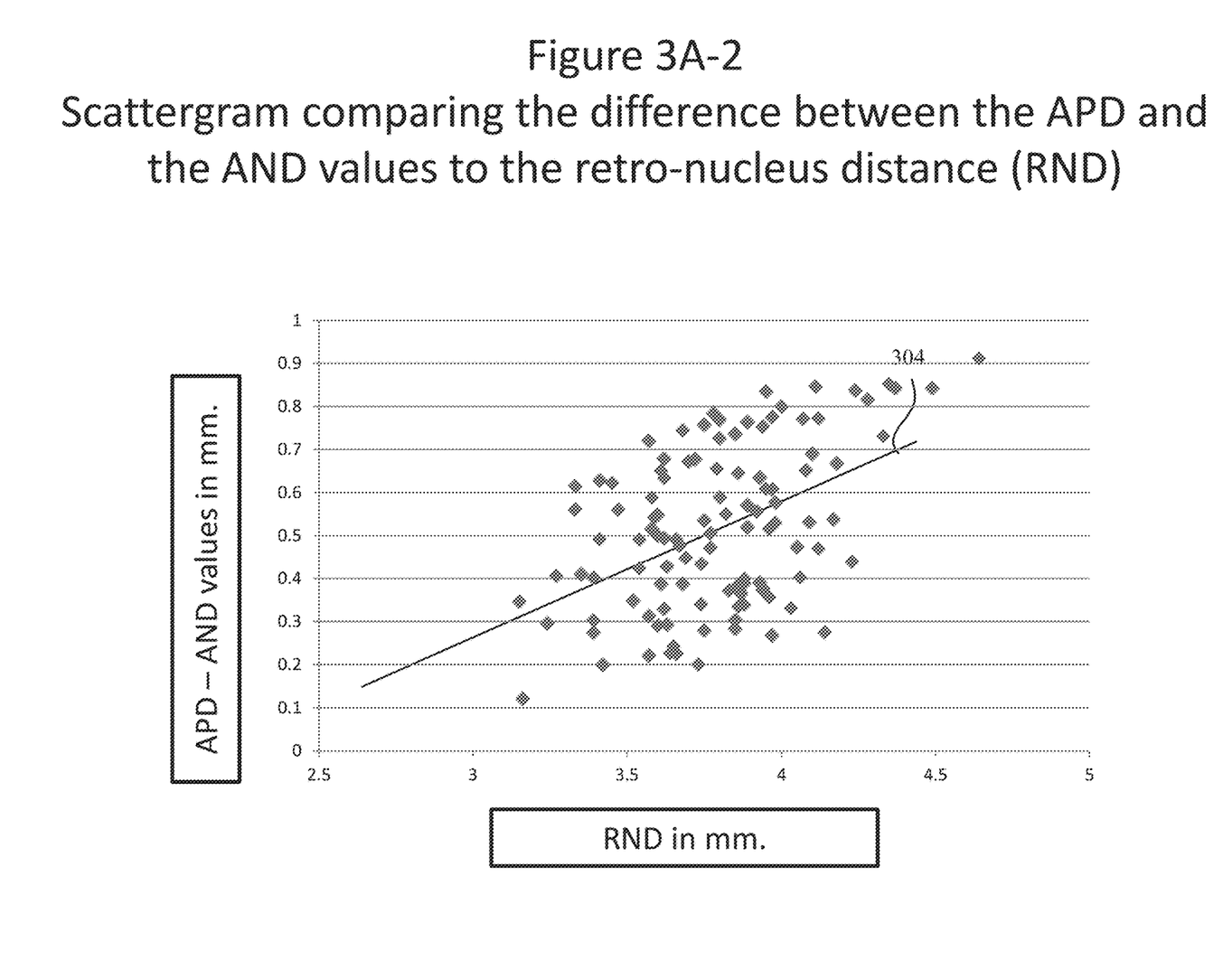
Figure 3B:
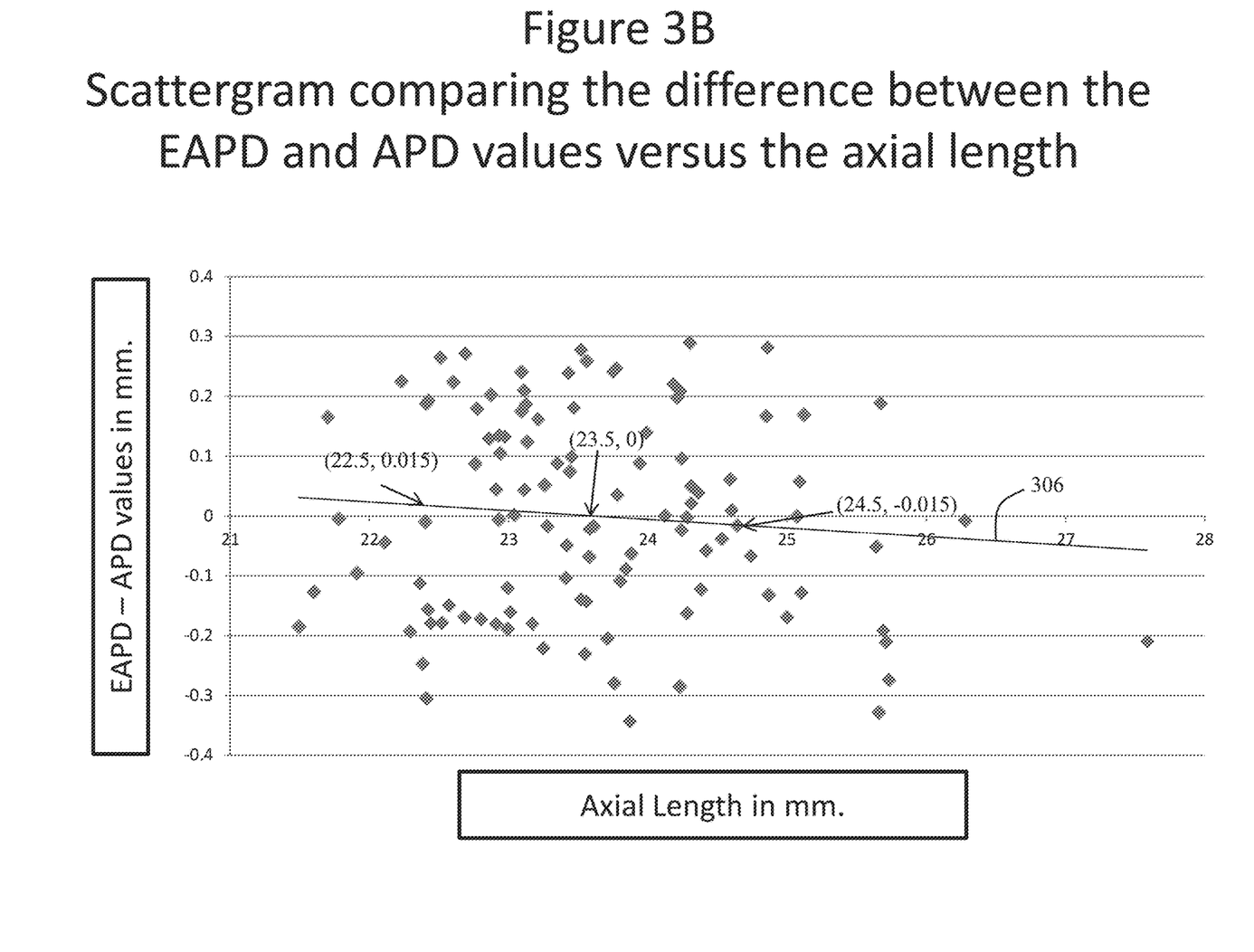
FIG. 3B is a non-limiting, exemplary illustration of scattergram chart, comparing the differences between the EAPD and the APD values versus the AL in accordance with one or more embodiments of the present invention.
Figure 3C:
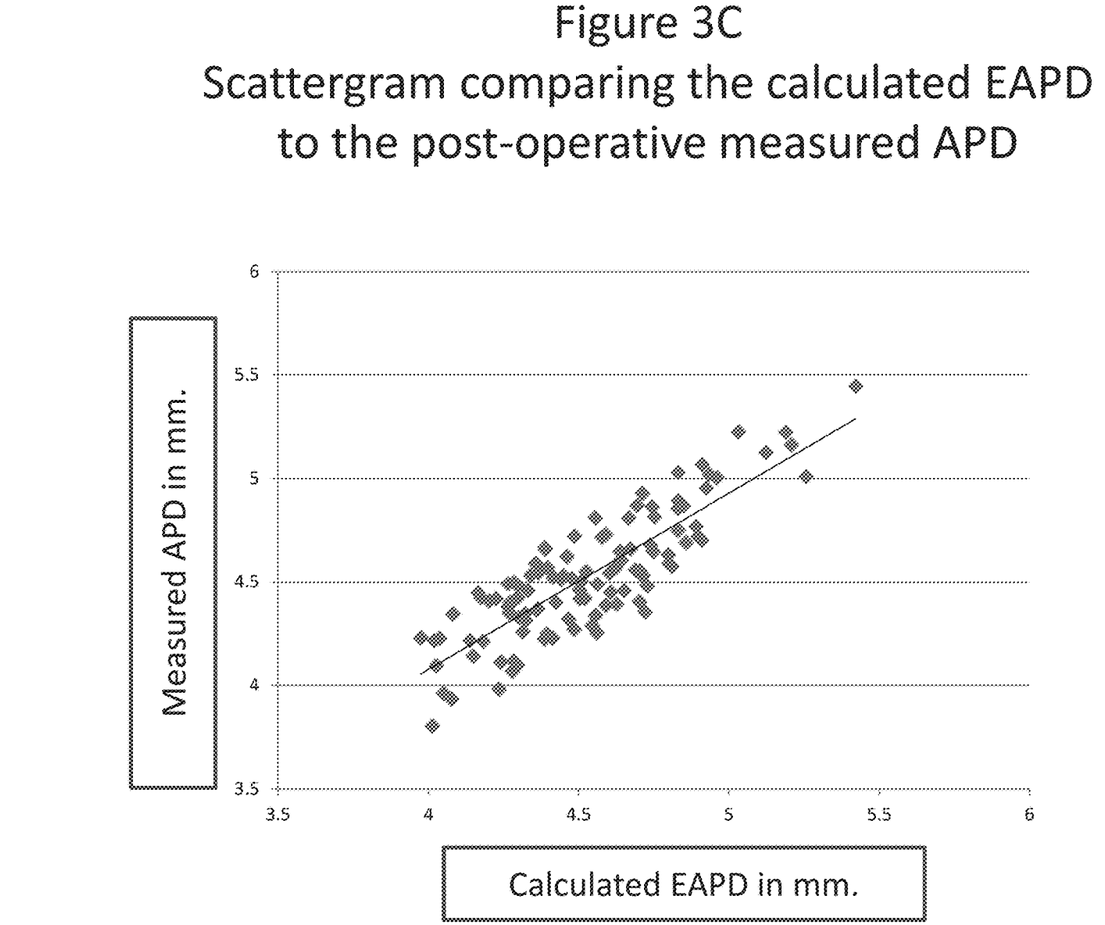
FIG. 3C is a non-limiting, exemplary illustration of scattergram chart, comparing the calculated EAPD to the postoperative measured APD in accordance with one or more embodiments of the present invention.

FIG. 3A-1 is a non-limiting, exemplary illustration of scattergram chart, comparing the differences between the post-operative APD and the pre-operative AND values to the NT, with the Y-axis showing measurements of APD-AND difference values in millimeters, and the X-axis showing the measurements of the NT in mm. FIG. 3A-2 is a non-limiting, exemplary illustration of scattergram chart, comparing the differences between the post-operative APD and the pre-operative AND values to the RND, with the Y-axis showing measurements of APD-AND difference values in millimeters, and the X-axis showing the measurements of the RND in mm. FIG. 3B is a non-limiting, exemplary illustration of scattergram chart, comparing the differences between the EAPD and the APD values versus the AL, with the Y-axis showing measurements of EAPD-APD differences values in millimeters, and the X-axis showing the measurements of the AL in mm. FIG. 3C is a non-limiting, exemplary illustration of scattergram chart, comparing the calculated EAPD to the post-operative measured APD, with the Y-axis showing measurements of APD values in millimeters, and the X-axis showing the calculated EAPD in mm.

The data from the scattergram charts of FIGS. 3A-1 to 3C was evaluated to derive the Pearson-Moment Correlation Coefficients R, which are tabulated in Table 1 and Table 2 below, resulting in the following EAPD formulas, the derivations of which are further detailed below.

$$EAPD = AND + 0.386 NT - 0.749 + 0.015 (AL - 23.50) \quad (5)$$

$$EAPD = AND + 0.315 RND - 0.677 + 0.015 (AL - 23.50) \quad (6)$$

The predicted refractive error is calculated as the difference between the predicted refraction (preoperative) and the actual measured refraction (postoperative). A positive value indicates the $IOL_{EP}$ would have left the eye more hyperopic than expected, and a negative value indicates that the $IOL_{EP}$ would have left the eye more myopic than expected.

As tabulated in Tables 1 and 2, regression equations compared the post-operative anterior pseudophakic distance (APD) to the different pre-operative measurements. Table 1 shows the correlation coefficient (R) of these different individual relations. Table 1 below establishes that the highest correlation is between the post-operative APD measurement and the pre-operative AND measurement (R=0.81).

As indicated in Table 2, the best fit (R=0.85) was obtained when APD was correlated to the AND, NT and AL (equation 1a) or AND, RND and AL (equation 1b). In other words, the equations 1a and 1b are statistically equal.

TABLE 1

Correlation co-efficient Value (R) between the post-operative anterior pseudophakic distance (APD) and the different pre-operative measurements to establish main correlating factor

| Using a single regression equation | R Value |
|---|---|
| APD vs. AL | 0.47 |
| APD vs. ACD | 0.66 |
| APD vs. LT | 0.01 |
| APD vs. K | 0.20 |
| APD vs. NT | 0.16 |
| APD vs. RND | 0.11 |
| APD vs. AND | 0.81 |

TABLE 2

Correlation co-efficient Value (R) between the post-operative anterior pseudophakic distance (APD) and the combination AND and NT, and the combination AND and RND

| Using a sequential regression equation | R Value |
|---|---|
| APD vs. AND | 0.81 |
| APD vs. AND and NT | 0.84 |
| APD vs. AND and RND | 0.84 |
| APD vs. AND, NT, and AL | 0.85 |
| APD vs. AND, RND, and AL | 0.85 |

The surgically implanted IOL will be located in the space occupied by the nucleus. In other words, the post-operative APD value is the sum of the AND value and a portion of the lens nuclear thickness (NT). To evaluate this relationship, the difference between the post-operative APD and the pre-operative AND values is compared to the nucleus thickness (NT). As indicated above, FIG. 3A-1 is a non-limiting, exemplary illustration of scattergram chart, comparing the differences between the APD and the pre-operative AND values to the NT, with the Y-axis showing measurements of APD-AND difference values in millimeters, and the X-axis showing the measurements of the NT in mm. It is well known that the linear regression equation may be represented by:

$$Y=aX+b, \quad (7)$$

where "a" and "b" are constants. In FIG. 3A-1, the line equation of the illustrated trend line 302 may be represented (and in fact calculated) as a linear regression equation:

$$Y=0.386X-0.749, \quad (8)$$

which is determined using the data values of the plotted data. The present invention substitutes the difference (APD-AND), the Y-axis of the graph of FIG. 3A-1, for the Y variable in linear regression equation (8), and the NT, which is the X-axis of the graph of FIG. 3A-1, for the X variable in the linear regression equation (8) with the "a" and "b" as the two constants as follows:

$$APD-AND=0.386NT-0.749 \quad (9).$$

Solving the above equation (9) for APD results in the following equation (10):

$$APD=AND+0.386NT-0.749 \quad (10)$$

Equation (10) can then be used as a way to estimate pre-operatively the APD value (the EAPD) in equation (1a).

Similarly with respect to equation (1b), the surgically implanted IOL is located in the space occupied by the nucleus and the posterior cortex, the space that is labeled the retro-nucleus distance (RND). In other words, the post-operative APD value is the sum of the AND value and a portion of the retro-nucleus distance (RND). To evaluate this relationship, the difference between the post-operative APD and the pre-operative AND values is compared to RND. As indicated above, FIG. 3A-2 is a non-limiting, exemplary illustration of scattergram chart, comparing the differences between the post-operative APD and the pre-operative AND values to the RND, with the Y-axis showing measurements of APD-AND difference values in millimeters, and the X-axis showing the measurements of the RND in mm. Using the linear regression equation (7) in view of the data in FIG. 3A-2, the line equation of the illustrated trend line 304 may be represented (and in fact calculated) as the following linear regression equation:

$$Y=0.315X-0.677, \quad (11)$$

which is determined using the data values of the plotted data. The present invention substitutes the difference (APD-AND), the Y-axis of the graph of FIG. 3A-2, for the Y variable in linear regression equation (11), and the RND, which is the X-axis of the graph of FIG. 3A-2, for the X variable in the linear regression equation (11) with the "a" and "b" as the two constants (of equation (7)) as follows:

$$APD-AND=0.315RND-0.677 \quad (12).$$

Solving the above equation (12) for APD results in the following equation (13):

$$APD=AND+0.315RND-0.677. \quad (13)$$

Equation (13) can then be used as a way to estimate pre-operatively the APD value (the EAPD) in equation (1b).

The inventor also postulates that the axial length AL has a slight influence on these equations, especially in the very short and the very long eyes. To evaluate how the axial length affects the EAPD value, the difference between EAPD and APD is compared to the axial length measurement. FIG. 3B is a scattergram comparing the difference between the calculated EAPD and the measured APD value (EAPD−APD) to the axial length (AL). In FIG. 3B, it is readily apparent that if EAPD is equal to the APD for all of the values of AL, then all of the ordinate values (or the Y values) of all of the (X, Y) points defining the trend line 306 will be zero (or (X, 0) or (AL, 0)). This means that the value of AL (indicated as the abscissa) is not relevant for cases that EAPD and APD are equal. However, as illustrated, the trend line 306 is not horizontal but sloped at some angle, with only one single zero crossing (ZC) point ($AL_{ZC}$, 0). Accordingly, in view of the data plotted, the zero-crossing point of the illustrated trend line 306 may be interpreted as the single point ($AL_{ZC}$, 0) where the average of the EAPD values and the average of the APD values are equal. This means that at the zero crossing of the trend line 306 the Y value or the ordinate value of the zero crossing point ($AL_{ZC}$, Y=0) is defined as:

$$0=EAPD_{AVG}-APD_{AVG}, \quad (14)$$

In this non-limiting exemplary instance (with ninety patients), the zero-crossing point for the trend line 306 is calculated to be an $AL_{ZC}$ value of 23.5 mm, giving the zero crossing point the full value of (23.5, 0).

As further indicated by FIG. 3B, portions of the trend line 306 that are above the zero crossing indicate that the EAPD values are higher than the actual APD values, which means that the EAPD has been over-estimated for shorter eyes (the distance of which is determined by the AL (represented as the abscissa)). Further, portions of the trend line 306 that are below the zero crossing indicate that the EAPD values are less than the actual APD values, which means that the EAPD has been under-estimated for longer eyes (the distance of which is determined by the AL).

To correct the estimations (so that EAPD=APD), the over-estimated EAPD values (those that are above the zero crossing) must be decreased and the under-estimated EAPD values (those below the zero-crossing) must be increased. The compensation value by which the EAPD is increased or decreased to compensate for over or under estimations of EAPD is determined as follows:

$$\frac{Y_{ZC} + Y}{|AL_{ZC} - AL|} \tag{15}$$

Where $AL_{ZC}$ is the AL value of the trend line 306 at its zero crossing, $Y_{ZC}$ is zero (EAPD=APD) value for the ordinate at zero crossing of the trend line 306, and AL is another abscissa value on the trend line 306, Y is another ordinate value on the trend line 306, with the denominator of equation (15) taking the absolute value of the difference between two points on the trend line 306 because a negative length is not possible. In general, since the abscissa representing the AL measurements is given in integers (or whole numbers) in millimeters length, $AL_{ZC}$ would be 23.5 and $Y_{ZC}$ would be zero (where EAPD=APD). Tracing the trend line 306 starting from zero-crossing at point (23.5, 0) and moving a single millimeter along the abscissa above the zero crossing would identify the trend line point:

$$\frac{0 + 0.015}{|23.5 - 22.5|} = \frac{0.015}{1} \tag{16}$$

According, the EAPD has been over-estimated by 0.015 (a positive value), requiring an equal compensation reduction to set the EAPD=APD. Tracing the trend line 306 starting from zero-crossing at point (23.5, 0) and moving a single millimeter below the zero crossing would identify the trend line point:

$$\frac{0 - 0.015}{|23.5 - 24.5|} = \frac{-0.015}{1} \tag{17}$$

According, the EAPD has been under-estimated by 0.015 (a negative value), requiring an equal compensation increase to set the EAPD=APD. Therefore, in this non-limiting exemplary instance, the amount by which the over-estimated EAPD must be decreased is found to be approximately 0.015 mm and the amount by which the under-estimated EAPD must be increased is found to be approximately 0.015 mm. Accordingly, the first EAPD equation (1a) that is based on the AND, NT and AL measurements becomes:

$$EAPD=AND+0.386NT-0.749+0.015(AL-23.50) \tag{18a}$$

It should be noted that the constants 0.386 and −0.749 may vary with different IOL models, manufacturers, surgical procedures, and many other factors. The equation (18) includes the compensation values "0.015 (AL−23.50)" for over or under estimation, which sets the EAPD=APD for the non-limiting example of ninety patients.

By solving the arithmetic calculations, Equation 18a can be re-written:

$$EAPD=-1.1015+AND+0.386NT+0.015AL \tag{18b}$$

In equation (18b), −1.1015, 1, 0.386 and 0.015 become the $S_1$, $S_2$, $S_3$ and the $S_4$ constants that characterize Equation (1a).

The second EAPD equation (1b) that is based on the AND, RND and AL measurements becomes:

$$EAPD=AND+0.315RND-0.677+0.015(AL-23.50) \tag{19a}$$

As with equation (18a), in the above equation (19a), the constants 0.315 and −0.677 may vary with different IOL models, manufacturers, surgical procedures, and many other factors. The equation (19) includes the compensation values "0.015 (AL−23.50)" for over or under estimation, which sets the EAPD=APD for the non-limiting example of ninety patients.

By solving the arithmetic calculations, Equation 19a can be re-written:

$$EAPD=-1.0295+AND+0.315RND+0.015AL \tag{19b}$$

In equation (19b), −1.0295, 1, 0.315 and 0.015 become the $W_1$, $W_2$, $W_3$ and the $W_4$ constants that characterize Equation (1b).

FIG. 3C is a scattergram comparing the calculated EAPD to the post-operative measured APD distance (using either of the equations (18) and or (19)). Using the trend line illustrated in FIG. 3C, the correlation coefficient (using AL) is determined to be R=0.850 (tabulated in Table 2 above), which is an improvement from R=0.840 (without using AL—tabulated in Table 2 above). In this example, the constants for both equations (18) and (19) were derived from one specific IOL make/model from one specific manufacturer. IOL's anterior radius of curvature, its posterior radius of curvature and its thickness determine the power of an IOL. Different IOL make/models will have variations in the anterior or posterior curvatures or in its thickness, which will affect the values of the constants in equations (1a) and (1b). Depending on the magnitude of the differences with the IOL used in this example, it is anticipated that the $S_2$, $S_3$, $S_4$ and the $W_2$ $W_3$ $W_4$ constants (for the respective equations (1a) and (1b)) will vary by up to approximately 5% (per constant), which in turn will affect the calculation of $S_1$ and $W_1$ by up to approximately 10% (cumulative). It should be noted that the constants in equations (1a) and (1b) may also vary and be affected depending on many other factors, non-limiting, non-exhaustive listing of examples of which may include the type of IOL used (as mentioned), the type and the manner in which an ophthalmic surgery is performed, the experience of the physician performing the surgery, whether the phacoemulsification was uneventful or had complications, and etc.

The accuracy of the new formula's (equations 1a and 1b) IOL power calculations is evaluated by comparing them with the four most commonly used intraocular lens power formulas, which are the SRK/T, Holladay 1, Hoffer Q and the Haigis. These formulas are programmed within most biometry/keratometry units and on different computer programs. All four formulas are based on geometric optics and use thin lens vergence equations in which each lens is reduced to a power at its principle plane. The position of each principle plane depends on the lens power and its anterior and posterior curvatures. Although all four formulas use the same optical principles, they differ from each other in the way they estimate the position of the surgically implanted IOL, a value often referred to as the Estimated Lens Position (ELP).

Each of these formulas uses a different algorithm based on certain pre-operative measurements. The SRK/T, Holladay 1 and the Hoffer Q base their algorithm on the axial length of the eye and the radius of curvature of the anterior corneal surface. These ELP values do not represent the true position of the IOL. Instead, these algorithms were obtained by analyzing clinical data and adjusting the calculated resultant refractive error in these cases to match the actual post-operative refractive result. The calculated ELP values are labeled the formulas' constants, i.e. the "A" constant for the SRK/T formula, the "SF" constant for the Holladay 1 formula and the "pACD" constant for the Hoffer Q formula. Although most manufacturers give a specific "A" constant to each IOL model, surgeons are advised to "personalize" the constants by reviewing a minimum of 20 cases and adjusting the constants until the mean difference between the calculated resultant refractive error and the actual post-operative refractive result becomes zero.

Using the thick lens algorithm for IOL power calculation, Haigis1 calculated an IOL position estimate by means of multiple regression analysis performed on preoperative data. The highest correlation coefficient (0.68) was with the anterior chamber depth, a result that closely parallels ours (0.66). In his formula, Haigis estimates the postoperative ACD as a function of the preoperative ACD and the AL.

Table 3 is an evaluation of the EAPD in accordance with the present invention (row 1) and used within the IOL power formula (Equations 1a and or 1b) compared with other commonly used formulas.

Although the invention has been described in considerable detail in language specific to structural features and or method acts, it is to be understood that the invention defined in the appended claims is not necessarily limited to the specific features or acts described. Rather, the specific features and acts are disclosed as exemplary preferred forms of implementing the claimed invention. Stated otherwise, it is to be understood that the phraseology and terminology employed herein, as well as the abstract, are for the purpose of description and should not be regarded as limiting. Therefore, while exemplary illustrative embodiments of the invention have been described, numerous variations and alternative embodiments will occur to those skilled in the art. For example, the new measurements used to establish the Equations 1a and 1b were made by optical biometry using the LENSTAR LS-900 biometer from HAAG-STREIT, INC. More specifically, these newly described measurements include the anterior cortical distance (ACX), nucleus thickness (NT), posterior cortical distance (PCX), ante nucleus distance (AND) and the retro nucleus distance (RND). Such measurements can also be made with other optical biometers, ultrasound units, optical coherence tomography (OCT) units and other one-dimensional, two-dimensional or three-dimensional imaging units. Further, the intraocular lens power calculation formula uses thin lens optics. Such calculations can also use thick lens optics, ray-tracing and different other computerized programs to calculate the IOL power. Such variations and alternate embodiments are contemplated, and can be made without departing from the spirit and scope of the invention.

It should further be noted that throughout the entire disclosure, the labels such as left, right, front, back, top, bottom, forward, reverse, clockwise, counter clockwise, up, down, or other similar terms such as upper, lower, aft, fore, vertical, horizontal, oblique, proximal, distal, parallel, perpendicular, transverse, longitudinal, etc. have been used for convenience purposes only and are not intended to imply

TABLE 3

Prediction errors with the present formula compared to the errors obtained with the Haigis, Hoffer Q, Holladay 1, and SKR/T formulas

| Formula | Med AE | Range | Prediction errors (% of patients) | | |
|---|---|---|---|---|---|
| | | | Within +/−0.50 D | Within +/−1.00D | Over 1.00D |
| Present Invention (Eq 1a and or 1b) | 0.30 | −1.01 to 0.98 | 71 (78.9%) | 89 (98.9%) | 1 (1.1%) |
| Haigis | 0.37 | −1.40 to 1.30 | 64 (71.1%) | 86 (95.5%) | 4 (4.4%) |
| Hoffer Q | 0.35 | −1.11 to 1.11 | 57 (63.3%) | 88 (97.8%) | 2 (2.2%) |
| Holladay 1 | 0.36 | −1.10 to 1.08 | 62 (68.9%) | 88 (97.8%) | 2 (2.2%) |
| SRK/T | 0.35 | −1.12 to 1.01 | 62 (68.9%) | 88 (97.8%) | 3 (3.3%) |

Table 3 shows the prediction errors with the present formula (equations 1a and or 1b) compared to the errors obtained with the Haigis, Hoffer Q, Holladay and SRK/T formulas. The accuracy of the new formula's IOL power calculations (equations 1a or 1b) is evaluated by comparing its median absolute error (MedAE) to the ones obtained with the other formulas. The median values are reported for the absolute prediction errors instead of the mean values because these absolute values do not fit a Gaussian curve distribution. The MedAE was noted to be lower with the present formula compared to the other formulas. Also, the percentage of patients with an accuracy of within +/−0.50 D+/−1.00 D was higher with the present formula (equations 1a or 1b) compared to the other formulas.

any particular fixed direction or orientation. Instead, they are used to reflect relative locations and/or directions/orientations between various portions of an object.

In addition, reference to "first," "second," "third," and etc. members throughout the disclosure (and in particular, claims) is not used to show a serial or numerical limitation but instead is used to distinguish or identify the various members of the group.

In addition, any element in a claim that does not explicitly state "means for" performing a specified function, or "step for" performing a specific function, is not to be interpreted as a "means" or "step" clause as specified in 35 U.S.C. Section 112, Paragraph 6. In particular, the use of "step of," "act of," "operation of," or "operational act of" in the claims herein is not intended to invoke the provisions of 35 U.S.C. 112, Paragraph 6.

What is claimed is:

1. A method for determining preoperative estimation of postoperative intraocular lens position of an intraocular lens, comprising:
an optical biometric machine that determines:
an axial length (AL) of an eye which is a distance from an anterior surface of a cornea of the eye along an optical axis of the eye to an anterior surface of a retina of the eye within a fovea region of the eye, with the optical axis being a reference line along which light propagates through the eye;
an Ante-Nucleus Distance (AND) of the eye, which is a distance from the anterior surface of cornea of the eye along the optical axis of the eye to an anterior surface of a natural lens nucleus of the eye; and
a Retro-Nucleus Distance (RND), which is a distance from the anterior surface of the natural lens nucleus of the eye to a posterior surface of a natural lens capsule of the eye;
with an Estimated Anterior Pseudophakic Distance (EAPD) for position of the intraocular lens is calculated in accordance with:

EAPD=$W_1$+($W_2$×AND)+($W_3$×RND)+($W_4$×AL),

Where $W_1$, $W_2$, $W_3$, and $W_4$ are constant coefficients;
wherein:
an intraocular estimated power $IOL_{EP}$ based on a location of the intraocular lens determined by the Estimated Anterior Pseudophakic Distance (EAPD) is derived by:

$$IOL_{EP} = \frac{n_{AH}}{AL - EAPD} - \frac{1}{\frac{1}{K + R_C} - \frac{EAPD}{n_{AH}}}$$

where:
$n_{AH}$ is a index of refraction for the aqueous humor;
K is corneal power; and
$R_C$ is refractive error at a corneal plane.

2. The method for determining preoperative estimation of postoperative intraocular lens position of an intraocular lens as set forth in claim 1, wherein:
AND is determined as follows:

AND=ACD+*ACX*;

where:
ACD is the Anterior Chamber Depth of the eye defined by a distance from the anterior surface of the cornea of the eye along the optical axis of the eye to an anterior surface of a natural lens of the eye, which is an anterior surface of a lens capsule of the eye; and
ACX is the Anterior Cortical Space of the eye defined by a distance from the anterior surface of the natural lens of the eye, which is the anterior surface of the lens capsule of the eye, along the optical axis of the eye to the anterior surface of the natural lens nucleus of the eye.

3. The method for determining preoperative estimation of postoperative intraocular lens position of an intraocular lens as set forth in claim 1, where:
RND is determined as follows:

RND=NT+*PCX*;

where:
NT is defined by a distance measured along the optical axis of the eye from the anterior lens nucleus surface of the eye to a posterior lens nucleus surface of the natural lens of the eye;
PCX is the Posterior Cortical Space defined by a distance from the posterior surface of the natural lens nucleus of the eye along the optical axis of the eye to the posterior surface of the lens of the eye, which is the posterior surface of the lens capsule of the eye.

4. The method for determining preoperative estimation of postoperative intraocular lens position of an intraocular lens as set forth in claim 3, where:
NT is determined as follows:

NT=LT-*PCX*-*ACX* where:
LT is defined as a distance measured along the optical axis from an anterior lens capsule surface to a posterior lens capsule surface of the natural lens, which includes the lens cortex and the lens nucleus;
PCX is a Posterior Cortical Space defined by a distance from a posterior surface of the natural lens nucleus along the optical axis of the eye to a posterior surface of the natural lens, which is a posterior surface of the lens capsule; and
ACX is an Anterior Cortical Space defined by a distance from the anterior surface of the natural lens, which is the anterior surface of the lens capsule along the optical axis of the eye to the anterior surface of the natural lens nucleus.

5. The method for determining preoperative estimation of postoperative intraocular lens position of an intraocular lens as set forth in claim 1, where:
RND is determined as follows:

RND=LT-*ACX* where:
LT is defined as a distance measured along the optical axis from an anterior lens capsule surface to a posterior lens capsule surface of the natural lens, which includes lens cortex of the eye and lens nucleus of the eye; and
ACX is an Anterior Cortical Space defined by a distance from the anterior surface of the natural lens, which is the anterior surface of the lens capsule along the optical axis of the eye to the anterior surface of the natural lens nucleus.

6. The method for determining preoperative estimation of postoperative intraocular lens position of an intraocular lens as set forth in claim 1, wherein:
constant coefficients $W_1$, $W_2$, $W_3$, and $W_4$ are statically derived using linear regression.

7. The method for determining preoperative estimation of postoperative intraocular lens position of an intraocular lens as set forth in claim 1, wherein:
constant coefficients $W_1$, $W_2$, $W_3$, and $W_4$ are statically derived using one of a linear, single, and sequential regressions.

8. The method for determining preoperative estimation of postoperative intraocular lens position of an intraocular lens as set forth in claim 1, further comprising:
determining a refractive power of a cornea of the eye; and
measuring Anterior Chamber Depth of the eye, which is defined as a distance from the anterior surface of the cornea of the eye along the optical axis of the eye to an anterior surface of a natural lens of the eye, which is an anterior surface of the lens capsule of the eye.

9. The method for determining preoperative estimation of postoperative intraocular lens position of an intraocular lens as set forth in claim 1, where:
the refractive power of cornea is determined by:
measuring a radius of curvature of the cornea (CR); and
converting the cornea radius into a corneal refractive power K using index of refraction.

10. The method for determining preoperative estimation of postoperative intraocular lens position of an intraocular lens as set forth in claim 1, wherein:
$R_C=0$ is used to calculate $IOL_{EP}$ for emmetropia, with $IOL_{EP}$ for ametropia calculated using a spectacle refraction $Rs=R_C/(1+0.012R_C)$.

11. A method for determining preoperative estimation of postoperative intraocular lens position of an intraocular lens, comprising:
determining an axial length (AL) of an eye which is a distance from an anterior surface of a cornea of the eye along an optical axis of the eye to an anterior surface of a retina of the eye within a fovea region of the eye, with the optical axis being a reference line along which light propagates through the eye;
determining an Ante-Nucleus Distance (AND) of the eye, which is a distance from the anterior surface of cornea of the eye along the optical axis of the eye to an anterior surface of a natural lens nucleus of the eye; and
determining a Retro-Nucleus Distance (RND), which is a distance from the anterior surface of the natural lens nucleus of the eye to a posterior surface of a natural lens capsule of the eye;
with an Estimated Anterior Pseudophakic Distance (EAPD) for position of the intraocular lens is calculated in accordance with:

$EAPD=W_1+(W_2\times AND)+(W_3\times RND)+(W_4\times AL)$,

Where $W_1$, $W_2$, $W_3$, and $W_4$ are constant coefficients;
wherein: AND, RND, and AL is determined using an optical biometric machine;
where:
RND is determined as follows:

$RND=LT-ACX$ where:
LT is a natural lens thickness and is defined as a distance measured along the optical axis from an anterior lens capsule surface to a posterior lens capsule surface of the natural lens, which includes lens cortex of the eye and lens nucleus of the eye; and
ACX is an Anterior Cortical Space defined by a distance from the anterior surface of the natural lens, which is the anterior surface of the lens capsule along the optical axis of the eye to the anterior surface of the natural lens nucleus.

12. A method for determining preoperative estimation of postoperative intraocular lens position of an intraocular lens, comprising:
determining an axial length (AL) of an eye which is a distance from an anterior surface of a cornea of the eye along an optical axis of the eye to an anterior surface of a retina of the eye within a fovea region of the eye, with the optical axis being a reference line along which light propagates through the eye;
determining an Ante-Nucleus Distance (AND) of the eye, which is a distance from the anterior surface of cornea of the eye along the optical axis of the eye to an anterior surface of a natural lens nucleus of the eye; and
determining a Retro-Nucleus Distance (RND), which is a distance from the anterior surface of the natural lens nucleus of the eye to a posterior surface of a natural lens capsule of the eye;
with an Estimated Anterior Pseudophakic Distance (EAPD) for position of the intraocular lens is calculated in accordance with:

$EAPD=W_1+(W_2\times AND)+(W_3\times RND)+(W_4\times AL)$,

Where $W_1$, $W_2$, $W_3$, and $W_4$ are constant coefficients;
wherein:
RND is determined as follows:

$RND=NT+PCX$;

where:
NT is defined by a distance measured along the optical axis of the eye from the anterior lens nucleus surface of the eye to a posterior lens nucleus surface of the natural lens of the eye;
PCX is the Posterior Cortical Space defined by a distance from the posterior surface of the natural lens nucleus of the eye along the optical axis of the eye to the posterior surface of the lens of the eye, which is the posterior surface of the lens capsule of the eye; and
wherein:
an intraocular estimated power $IOL_{EP}$ based on a location of the intraocular lens determined by the Estimated Anterior Pseudophakic Distance (EAPD) is derived by:

$$IOL_{EP} = \frac{n_{AH}}{AL-EAPD} - \frac{1}{\frac{1}{K+R_C} - \frac{EAPD}{n_{AH}}}$$

where:
$n_{AH}$ is a index of refraction for the aqueous humor;
K is corneal power; and
$R_C$ is refractive error at a corneal plane.

* * * * *